US005701256A

United States Patent [19]
Marr et al.

[11] Patent Number: 5,701,256
[45] Date of Patent: Dec. 23, 1997

[54] METHOD AND APPARATUS FOR BIOLOGICAL SEQUENCE COMPARISON

[75] Inventors: Thomas G. Marr; William I-Wei Chang, both of Huntington, N.Y.

[73] Assignee: Cold Spring Harbor Laboratory, Cold Spring Harbor, N.Y.

[21] Appl. No.: 455,654

[22] Filed: May 31, 1995

[51] Int. Cl.[6] .................................................. G06F 19/159
[52] U.S. Cl. .......................... 364/496; 382/128; 382/129
[58] Field of Search ........................... 364/496; 382/128, 382/129, 218; 436/89

[56] References Cited

U.S. PATENT DOCUMENTS

| | | | |
|---|---|---|---|
| 4,905,295 | 2/1990 | Sato | 382/197 |
| 4,979,226 | 12/1990 | Sato | 382/197 |
| 5,329,405 | 7/1994 | Hou et al. | 382/218 X |
| 5,523,208 | 6/1996 | Kohler et al. | 436/89 X |
| 5,538,897 | 7/1996 | Yates, III et al. | 436/89 |

OTHER PUBLICATIONS

P. Argos and M. Vingron, "Sensitive Comparison of Protein Amino Acid Sequences", in R.F. Doolittle ed *Methods in Enzymology* vol. 183:352–365 (1990).

Vingron and Waterman, "Parametic Sequence Alignments and Penalty Choice: Case Studies", Manuscript (1993).

Altshul, "Amino Acid Substitution Matrices from an Information Theoretic Perspective", *J. Molecular Biology* 219:555–565 (1991).

S.B. Needleman and C.E. Wunsch, "A General Method Applicable to the Search for Similarities in the Amino Acid Sequence of Two Proteins," *J. Molecular Biology* 48:443–453 (1970).

T.F. Smith and M.S. Waterman, "Identification of Common Molecular Subsequences", *J. Molecular Biology* 147:195–197 (1981).

O. Gotoh, "An Improved Algorithm for Matching Biological Sequences", *J. Molecular Biology* 162:705–708 (1982).

M.S. Waterman and M. Eggert, "A New Algorithm for Best Subsequence Alignments With Application to tRNA–rRNA Comparison", *J. Molecular Biology* 197:723–728 (1987).

M.S. Waterman, "Sequence Alignments", M.S. Waterman, ed. *Mathematical Methods for DNA Sequences*, CRC Press 53–92 (1989).

X. Huang and W. Miller, "A Time–Efficient, Linear–Space Local Similarity Algorithm", *Advances in Applied Mathematics* 12:337–357 (1991).

W.R. Pearson, "Searching Protein Sequence Libraries: Comparison of the Sensitivity and Selectivity of the Smith–Waterman and FASTA Algorithms", *Genomics* 11:635–650 (1991).

(List continued on next page.)

*Primary Examiner*—Edward R. Cosimano
*Attorney, Agent, or Firm*—Hamilton, Brook, Smith & Reynolds, P.C.

[57] ABSTRACT

A method and apparatus for comparing biological sequences from a known source of sequences, with a subject (query) sequence. The apparatus takes as input a set of target similarity levels (such as evolutionary distances in units of PAM), and finds all fragments of known sequences that are similar to the subject sequence at each target similarity level, and are long enough to be statistically significant. The invention device filters out fragments from the known sequences that are too short, or have a lower average similarity to the subject sequence than is required by each target similarity level. The subject sequence is then compared only to the remaining known sequences to find the best matches. The filtering member divides the subject sequence into overlapping blocks, each block being sufficiently large to contain a minimum-length alignment from a known sequence. For each block, the filter member compares the block with every possible short fragment in the known sequences and determines a best match for each comparison. The determined set of short fragment best matches for the block provide an upper threshold on alignment values. Regions of a certain length from the known sequences that have a mean alignment value upper threshold greater than a target unit score are concatenated to form a union. The current block is compared to the union and provides an indication of best local alignment with the subject sequence.

19 Claims, 3 Drawing Sheets

OTHER PUBLICATIONS

S.S. Sturrock and J.F. Collins, "MPsrch Version 1.3", Biocomputing Research Unit, University of Edinburgh, UK (1993).

P. Argos, et al., "Protein Sequence Comparison: Methods and Significance", *Protein Engineering* 4:375–383 (1991).

D.G. George, et al., "Mutation Data Matrix and Its Uses", In R.F. Doolittle, Ed. *Methods in Enzymology vol. 183 Academic Press*:333–351 (1990).

E.W. Myers, "An Overview of Sequence Comparison Algorithms in Molecular Biology", Technical Report TR91–29, Computer Science Department, University of Arizona, Tucson, Dec. (1991).

W.I. Chang and E.L. Lawler, "Approximate String Matching in Sublinear Expected Time", *Proceedings of the 31st Annual IEEE Symposium on Foundations of Computer Science* 116–124 Oct. (1990).

G.M. Landau and U. Vishkin, "Fast String Matching With k Differences", *J. Comp. Sys. Sci.* 37:63–78 (1988).

E. Ukkonen, "Finding Approximate Patterns in Strings", *J. Algorithms* 6:132–137 (1985).

E.W. Myers, "A Sublinear Algorithm for Approximate Keyword Searching", Technical Report TR90–25, Department of Computer Science, University of Arizona, Tucson, Sep. (1991).

X. Huang, "A Contig Assembly Program Based on Sensitive Detection of Fragment Overlaps", *Genomics* (1992).

S. Wu, et al., "A Sub–quadratic Algorithm for Approximate Limited Expression Matching", Technical Report TR92–36, Computer Science Dept., University of Arizona, Tucson, (Dec. 1992).

Wu and Manber, "Fast Text Searching Allowing Errors", *Comm. ACM* 35:83–91 (1992).

W.I. Chang, "Approximate Pattern Matching and Biological Applications", PH.D. Thesis, U.C. Berkeley, Aug. (1991) also available as Computer Science Division Reports UCB/CSD 91/653–654.

E.W. Myers, "Algorithmic Advances for Searching Biosequence Databases", *Computational Methods in Genome Research*, Plenum Press (1994).

P. H. Sellers, "The theory and Computation of Evolutionary Distances: Pattern Recognition", *J. Algorithms* 359–373 (1980).

W. B. Goad and M. I. Kanehisa, "Pattern Recognition in Nucleic Acid Sequences I, A General Method for Finding Local Homologies and Symmetrics", *Nucl. Acids Res.* 10:247–263 (1982).

P. H. Sellers, "Pattern Recognition in Genetic Sequences by Mismatch Density", *Bull Math. Biol.* 46:501–514 (1984).

Cuddihy, D. and Chang, W., "Sequence Analyst", *Cold Spring Harbor Annual Report*, pp. 1,3 (1995).

Chang, W. and Lampe, J., "Theoretical and Empirical Comparisons of Approximate String Matching Algorithms", *Proceedings of the Symposium on Combinatorial Pattern Matching, Springer–Verlag Lecture Notes in Computer Science*, 644:172–181 (1992).

Chang, W. and Lawler, E., "Sublinear Approximate String Matching and Biological Applications", *Algorithmica*, 12:327–344 (1994).

FIG. 3

METHOD AND APPARATUS FOR BIOLOGICAL SEQUENCE COMPARISON

GOVERNMENT SUPPORT

Work for the following disclosed invention was supported by the Department of Energy Grant DE-FG02-91ER61190 and National Institutes of Health Grant 1R01 HG0020301A1 to Thomas G. Marr. The Government may have certain rights in the invention.

RELATED PUBLICATIONS

The subject matter of the present invention is also discussed in the following publication. That publication is herein incorporated by reference.

"Approximate String Matching and Local Similarity" by William I. Chang and Thomas G. Marr, in *Proc. Symp. Combinatorial Pattern Matching '94*, Springer-Verlag Lecture Notes in Computer Science, 807:259–273 (June, 1994).

BACKGROUND OF INVENTION

It is often useful to compare new protein sequences with known sequences, such as from a sequence database. Usually one tries to determine what level of similarity is shared between the proteins in terms of structural and functional characteristics, and this determination is made by comparing the amino acid sequences of the proteins. Current understanding of the underlying processes of structure and function is not sufficient for a completely rigorous solution to this determination.

Nevertheless, two developments in particular have combined to produce a method that is reasonably rigorous and successful. The first of these attacks the central problem of assigning a score to the matching of a single pair of residues, according to chemical properties or statistical analysis of allowed mutations in known homologous sequences. The second is the rigorous treatment of optimal alignment of regions by dynamic programming.

The widely used point-accepted mutation (PAM) matrices of Dayhoff et al. ("A Model of Evolutionary Change in Proteins" in M. O. Dayhoff Ed. *Atlas of Protein Sequence and Structure* Vol. 5, Suppl. 3, pp. 345–352, 1979) were calculated on the basis of 1600 accepted point mutations in 71 groups of closely related proteins (<15% different). Qualitatively, each matrix reflects the intrinsic chemical classification of the twenty amino acids that are incorporated into proteins. This model of amino acid substitution assumes that the nonlethal mutations follow the same rate and distribution as in the original data, extrapolated to evolutionarily distant sequences and beyond. Generally, 50% identity over a putative domain (not the entire sequence) is considered extremely significant; in the PAM scale this corresponds to about 90 PAMs. Occasionally, a particular 33% identity (120 PAMs) alignment is claimed to be significant. But the standard or "default" scoring matrix is actually PAM 250, which in this model corresponds to the statistics of very distant (<20% identity) relationships. The use of PAM 250 is partly historical, and partly due to its empirical success at uncovering distant homologs. However, alignments produced by PAM 250 with low gap penalty are usually indistinguishable from noise. Although some known homologs are indeed 250 PAMs apart, in practice such relationships are nearly impossible to detect and to analyze, requiring much more sensitive methods (such as P. Argos and M. Vingron, "Sensitive Comparison of Protein Amino Acid Sequences," in R. F. Doolittle, ed *Methods in Enzymology* Vol. 183, pp. 352–365, 1990; Vingron and Waterman, "Parametric Sequence Alignments and Penalty Choice: Case Studies," Manuscript, 1993), and often with user-input.

Recently, Altshul (in "Amino Acid Substitution Matrices from an Information Theoretic Perspective," *J. Molecular Biology*, 219, pp. 555–565, 1991) has put forth a unifying theory of amino acid substitution matrices as devices for distinguishing a "target" frequency of aligned pairs from a "background" frequency of random amino acids. Specifically, the score for aligning a pair (x,y) has the form $S_{xy}=\log q_{xy}/P_x P_y$, where $q_{xy}$ is the characteristic frequency of pairing x with y among alignments representing homologs, and $P_x P_y$ is the frequency of pairing x with y by chance. The likelihood or "odds" ratio $q_{xy}/P_x P_y$ compares the probability of the event occurring under two alternative hypotheses; taking logarithm replaces multiplication with addition, so the total additive score of an alignment remains a "log-odds" score. A given scoring matrix is optimal for identifying homologs at its target frequency, against a background of similarities due to chance. That is, the $q_{xy}$ target frequencies can be calculated from the scoring matrix S and vice versa according to the foregoing equation.

It is extremely important to note the following distinction: PAM x is a scoring matrix; x PAMs is an evolutionary distance, defined by the target frequency of PAM x. In short, PAM x measures the likelihood that the aligned portion of two sequences are x PAMS apart evolutionarily. The best matrix for scoring an x PAMs alignment is PAM x, if x were known.

S. B. Needleman and C. E. Wunsch (in "A General Method Applicable to the Search for Similarities in the Amino Acid Sequence of Two Proteins," *J. Molecular Biology*, 48, pp. 443–453, 1970) formulated an explicit criterion for the optimality of a global alignment, scoring matches, mismatches, insertions, and deletions, and provided a quadratic time method. Here "global" can mean matching the entirety of one sequence (actually, all prefixes) against substrings of another. T. F. Smith and M. S. Waterman (in "Identification of Common Molecular Subsequences," *J. Molecular Biology*, 147, pp. 195–197, 1981) solved the local alignment problem by introducing a "zero trick": if an entry of the dynamic programming table is negative, then the optimal local alignment cannot go through this entry because the first part would lower the score; one may therefore replace it with zero, in effect cutting off the prefixes. (This simple trick is known in the computer science art as the maximum subvector method.) O. Gotoh (in "An Improved Algorithm for Matching Biological Sequences," *J. Molecular Biology*, 162, pp. 705–708, 1982) then showed that affine gap penalty (separate costs for number and lengths of gaps) is about as efficiently solved as is linear gap penalty, by using three states per cell (instead of the naive four). The identification of multiple, similar segments was achieved by M. S. Waterman and M. Eggert (in "A New Algorithm for Best Subsequence Alignments With Application to tRNA-rRNA Comparison," *J. Molecular Biology*, 197, pp. 723–728, 1987). Despite a slightly imprecise definition(i.e. procedural and nondeterministic under ties) of k best nonoverlapping alignments, this is "probably the most useful dynamic programming method for current problems in biology" (See M. S. Waterman, "Sequence Alignments," in M. S. Waterman, ed. *Mathematical Methods for DNA Sequences*, CRC Press, pp. 53–92, 1989). X. Huang and W. Miller (in "A Time-Efficient, Linear-Space Local Similarity Algorithm," *Advances in Applied Mathematics*, 12, pp. 337–357, 1991) introduced linear space optimizations that allow very large DNA sequences to be compared.

Although the Smith-Waterman method is apparently the best known method to date for comparing protein sequences, that method has drawbacks in terms of search time and arbitrary results. Using Smith-Waterman for database searching, a single search usually takes several hours. For this reason, faster heuristic methods (BLAST, FASTA) are far more popular than rigorous dynamic programming. The penalty of using a heuristic method is not only the potential loss of accuracy (which is incompletely understood), but also the loss of precision in describing the findings and nonfindings of a highly tweaked heuristic program. W. R. Pearson has tuned FASTA over many years to be a powerful tool, and in fact claims (in "Searching Protein Sequence Libraries: Comparison of the Sensitivity and Selectivity of the Smith-Waterman and FASTA Algorithms," *Genomics*, 11, pp. 635–650, 1991) that it is "as sensitive as" Smith-Waterman. Currently, Applicants' fast implementation of Gotoh-Smith-Waterman runs at about one-third the speed of FASTA (most sensitive setting, −o and ktup=1). It takes just ten minutes on a 200 Mhz DEC Alpha computer to compare a 400-residue sequence against the SwissProt database of about 15 million residues. The Email server blitz@EMBL-Heidelberg.de (see S. S. Sturrock and J. F. Collins, "MPsrch Version 1.3," Biocomputing Research Unit, University of Edinburgh, UK, 1993) is about 10 times faster, running on a 4,000-processor MasPar computer. The BLAST program is also very fast, but only finds gapless alignments.

As far as arbitrary results from the Smith-Waterman method: the "optimal" local alignment can have arbitrarily low (positive) unit score (mean score per aligned pair of amino acids or total score divided by alignment length). In fact, the Smith-Waterman method cannot be used to find only those alignments whose unit or average score is above a given threshold. Thus, the significance of a target alignment with the given unit score may be shadowed by alignments with higher total scores but are much too long or too short. This results in an erroneous finding of related sequences.

For example, a match of a particularly conserved amino acid residue among a family of proteins is more significant than another amino acid match shared by only two proteins. Thus, one would expect that such a significant match should cause a particular alignment to get a high unit score. However, the significance of this alignment may be shadowed by longer (or shorter) alignments with more (but not necessarily as significant) matches. This, results in an erroneous relative order of relation of local alignment.

One can compute from the given PAM x matrix the expected unit score (called "relative entropy") of its target frequency x PAMs.

| xPAM EVOLUTIONARY DISTANCE | PERCENT IDENTITY | EXPECTED UNIT SCORE (BITS) | MINIMUM LENGTH TO YIELD 30 BITS |
|---|---|---|---|
| 40 | 70 | 2.3 | 14 |
| 80 | 55 | 1.4 | 21 |
| 120 | 33 | 1.0 | 31 |
| 250 | 20 | .36 | 83 |

If the observed unit score of the alignment in question is much lower than the relative entropy (expected unit score), then the alignment must be much more distant than x PAMs. It is generally futile to look for alignments much more distant than x PAMs using PAM x as the scoring matrix. Instead, one should look for alignments with the right unit score (characteristic of x PAMs) as well as total score (at least 30 "bits" for database search)-but this is not possible using the Smith-Waterman method. The desired alignment can be "shadowed" by one that is higher scoring but also much longer. In a database search, Smith-Waterman will discover every sequence that contains an alignment of the desired total score. One may attempt to use the nonoverlapping suboptimal alignments method to generate all such alignments and apply the unit score test, but this does not work if the desired alignment is shadowed by one that does overlap it. Indeed, shadowing takes place even in the normal course of computing a Smith-Waterman dynamic programming matrix-the highest scoring local alignment ending at a given cell may not be one with the highest average.

To solve this problem, one can apply the Needleman-Wunsch method separately to every suffix of the query sequence, so alignments ending at a particular cell have a fixed length (defined to be the length of the query substring). The drawback is of course that this is cubic, though significant optimization is possible in practice. This is related to previous attempts at defining a distance-based optimal local alignment. An alternative approach is to subtract the relative entropy from each entry of the scoring matrix. This also has the effect of greatly enhancing the power of database filtering, at the risk of chopping alignments into short pieces, which must be combined in some way. It is noteworthy that much of the power of heuristic methods such as FASTA are derived from careful fine-tuning of such a step.

Useful surveys on this subject include Altshul (cited above), P. Argos et al., "Protein Sequence Comparison: Methods and Significance," *Protein Engineering*, 4:(1991) pp. 375–383; D. G. George et al., "Mutation Data Matrix and Its Uses," In R. F. Doolittle, Ed. *Methods in Enzymology Volume* 183, Academic Press (1990), pp. 333–351; and E. W. Myers, "An Overview of Sequence Comparison Algorithms in Molecular Biology", Technical Report TR91-29, Computer Science Department, University of Arizona, Tucson, September 1991.

SUMMARY OF THE INVENTION

The present invention formulates and solves the problem of local similarity in a new way, by adding a constraint on the unit score of matched fragments. This constraint filters out very long or very short alignments with unacceptably low similarity levels. The method of the current invention also proceeds faster than the Smith-Waterman method, obtaining comparable or better results two to ten times faster, and is implementable using inexpensive hardware. The present invention uses a text/pattern matching scheme to compute and store the best match between each possible short segment of known sequences (e.g., five amino acids) and the query sequence. The stored results are then used to bound the scores of local alignments and eliminate those alignments that are too short, or long but weak overall, i.e., have high match rates (high unit score) but a low average score (averaged over the length of the alignment). The invention method is applicable to sequence comparisons based on either similarity (e.g., scores assigned according to chemical properties of the twenty amino acids) or distance (e.g., the number of insertions, deletions or substitutions required to mutate one sequence fragment to another). Thus, the present invention allows for a more consistent and reliable characterization of the relative relatedness of proteins or other biological sequences.

In particular, the present invention provides computer apparatus for comparing biological sequences. The apparatus includes a source of known biological (protein) sequences, a computer filter and a comparison member. The source of known biological sequences is, for example, a database. The computer filter means filters out all possible alignments of the known sequences (or fragments thereof) having low average match when compared to a subject sequence (or fragments thereof). This filtering produces a remaining subset of the source of known sequences having alignments sufficiently matching the subject sequence on average. The comparison member is coupled to the computer means for comparing the subject sequence with each known sequence in the remaining subset to find a best match.

In the preferred embodiment, the computer filter includes processor means for dividing the subject sequence into overlapping blocks. Each block is sufficiently large to contain an alignment of length L from a known sequence. For each block, the processor means:

(i) compares the block with every possible short fragment (e.g., pentamers) in the known sequences and stores the results in a table, for example;

(ii) compares the block with known sequences using the above results to determine a set of upper bounds on alignment values;

(iii) from the known sequences, determines regions of at least length L that have a mean alignment value upper bound greater than (or equal to) a target threshold (e.g., relative entropy or expected unit score);

(iv) forms a union of the determined regions; and (v) compares the union with the block in a manner that produces an indication of best local alignment.

In one embodiment the processor means produces a local alignment score as the indication of best local alignment. In that case, when the local alignment score is greater than or equal to 20 bits (each bit represents a 2:1 odds that a match is not random) then the comparison member compares the subject sequence to the appropriate source sequence (i.e., the sequence formed of the determined regions in the subject union).

In accordance with one aspect of the present invention, the processor means determines regions from the known sequences of at least length L including rounding down to a multiple of 5.

Another object of the present invention is the use of evolutionary distance as a search (or comparison) target. The invention method is computationally rigorous to find all such targets in a practicable manner.

BRIEF DESCRIPTION OF THE DRAWINGS

The foregoing and other objects, features and advantages of the invention will be apparent from the following more particular description of preferred embodiments and the drawings in which like reference characters refer to the same parts throughout the different views. The drawings are not necessarily to scale, emphasis instead being placed upon illustrating the principles of the invention.

FIG. 3 illustrates comparison of two PAM scoring matrices.

DETAILED DESCRIPTION OF THE INVENTION

Figures 1A, 1B, 1C:
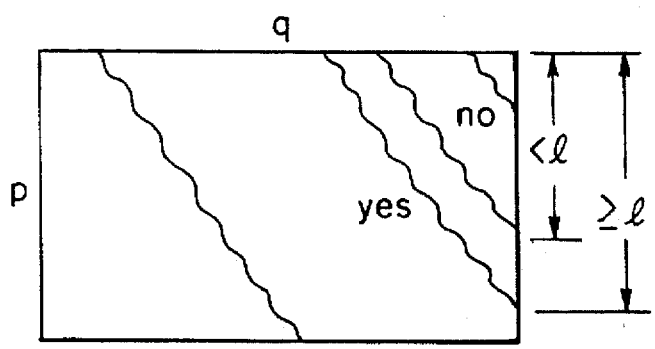
FIGS. 1a–1c illustrate pattern matching, overlap detection and redundancy detection, respectively.

Protein sequence comparisons are a subjective and time consuming process with potential for variable interpretation. Although generally, a high degree of matching among amino acid residues is significant, there are instances where a lower degree of matching over a larger region is more significant. The usefulness and effectiveness of a sequence comparison method depends upon the search criteria and sometimes the protein itself; some searches are too cumbersome to carry out with currently available methods because the data generated is not reliable but arbitrary in some instances. Some comparison methods are better suited to particular database searches than others, depending both on search criteria and user input. Further, the interpretation and classification of known protein sequences (e.g., structural and functional characteristics) in a database is subjective and inconsistent. Thus, the database is not necessarily correctly indexed or categorized for "easy" (straightforward) searching and comparison.

By way of background, pattern matching is one of the classical problems of computer science. Fast algorithms and tight lower bounds are known for the exact matching of a pattern (of size m) inside a text string (of size n), over some alphabet (of size b). The situation with nonexact, or approximate matching is less satisfactory. Until W. I. Chang and E. L. Lawler's ("Approximate String Matching in Sublinear Expected Time," *Proceedings of the 31st Annual IEEE Symposium on Foundations of Computer Science*, pp. 116–124, October 1990) sub-linear expected time filtering result for sublogarithmic-fraction error, approximate string matching was thought to be hard. The O(kn) method of G. M. Landau and U. Vishkin ("Fast String Matching With k Differences", *J. Comp. Sys. Sci.*, 37, pp. 63–78, 1988) for k differences was a breakthrough, but no better than classical dynamic programming when the error rate is a constant fraction of the pattern size. By relaxing the error rate requirement slightly, to $k<m/(\log_b m+O(1))$, Chang and Lawler found a method that is much faster on average for random text. (Subsequently several O(m/log m)-error filters have appeared, but one should make explicit the constant factor in the big-O notation; for example $m/3\log_b m$ is quite easy by hashing, but also rather weak.) This is achieved by filtering the text with a device called matching statistics (locally the longest exact match), and calling a dynamic programming subroutine only when the filter cannot prove that there is no match. In the present invention, applicants improve that result even further, to constant-fraction $k<\epsilon_b m$ error. This is the first algorithm for constant-fraction error matching that is significantly sub-quadratic (in face O(n) on average) and does not use exponential space, (E. Ukkonen, "Finding Approximate Patterns in Strings," *J. Algorithms*, 6, pp. 132–137, 1985), or an inverted index of the text (E. W. Myers, "A Sublinear Algorithm for Approximate Keyword Matching", Technical Report TR90-25, Computer Science Department, University of Arizona, Tucson, September 1991, $O(\epsilon m n^{f(\epsilon,b)} \log n)$ time). It will also be noted that the invention method is in fact optimal, i.e. meets a lower bound to within a constant factor.

Because it is easier to be rigorous with a distance (metric) than with a similarity (nonmetric), computer science has traditionally focused on distance measures, such as (Hamming) mismatch distance or (Levenshtein) edit distance. For these special measures, very efficient optimizations have been invented (several are surveyed in W. I. Chang and J. Lampe, "Theoretical and Empirical Comparisons of Approximate String Matching Algorithms," *Proc. Combinatorial Pattern Matching '92*, Tucson, Ariz., Apr. 29–May 1, 1992, Lecture Notes in Computer Science 644, Springer-Verlag, pp. 172–181). Currently the fastest method for edit distance (arbitrary k), called kn.clp, partitions columns of the dynamic programming matrix into segments containing increasing arithmetic progressions. By doing only one unit of work per segment, kn.clp achieves an observed speed of $O(kn/(\sqrt{b}-1))$, that is, much faster with larger alphabets. Further, there are extremely fast programs for motif finding (clp) where each position of the pattern can match several (chemically similar) amino acids or a variable length gap; redundancy detection (differ) where an error threshold is given; overlap detection (overlap) allowing some fraction error in the overlap.

That is, in "pattern matching", computation proceeds column by column. See FIG. 1A. The amount of work is proportional to the number of segments (run of consecutive integers). The empirically observed and conjectured average run length is $\sqrt{b}$, as exemplified by kn.clp discussed above. A special case of pattern matching is "overlap detection". See FIG. 1B. Using p as the subject pattern, overlap detection determines whether q contains p or a suffix of q matches a prefix of p (of length at least 1). This allows a constant fraction k/1 errors. Then q is used as the subject pattern and the overlap detection determines whether p contains q, or a suffix of p matches a prefix of q. On the other hand, "redundancy detection" is a scheme for edit distance, computed in alternating columns and rows. See FIG. 1C. The amount of work is proportional to the number of digits shown; each digit indicates a new segment (|or–). Cells that are deduced to be greater than the threshold are shown as \ and are not actually computed.

Example programs to perform the foregoing tasks include the following. The contig assembly program (CAP) of X. Huang, "A Contig Assembly Program Based on Sensitive Detection of Fragment Overlaps," *Genomics*, (1992) for the task of piecing together overlapping DNA fragments (with errors) is based on Chang and Lawler (cited above). S. Wu, U. Manber, E. W. Myers, "A Sub-quadratic Algorithm for Approximate Limited Expression Matching," Technical Report TR92-36, Computer Science Dept., University of Arizona, Tucson, (December 1992) describes a program similar to clp (its user interface is used by clp) that is even a bit faster when the machine has a large (512K) data cache. The agrep program of Wu and Manber, "Fast Text Searching Allowing Errors," *Comm. ACM*, 35, pp. 83–91 (1992) is also extremely fast at extracting records from unindexed databases.

Applicants realized that the combinatorial lemma used to prove the O(kn) average-case running time of kn.clp can be applied to a "bootstrapping" method described by W. I. Chang, in "*Approximate Pattern Matching and Biological Applications,*" PH.D. Thesis, U.C. Berkeley, August 1991 (also available as Computer Science Division Reports UCB/ CSD 91/653–654), to produce the constant-fraction-error optimality result mentioned above. Briefly, this method treats short ($\alpha.\log_b m$) segments of the text as patterns, and the original pattern as text. The best match between each segment and the entire original pattern is computed, and used to bound the local alignment. This generalizes and strengthens the matching statistics filtering method used by Chang and Lawler (cited above) to discard entire sections of the text. Only polynomial space $m^\alpha$ is required, where $\alpha$ is independent of m and n, but dependent on b and the error rate $\epsilon_b$. Interestingly, this new method is equally applicable to both distance and similarity. (Another, weaker adaptation to similarity measure is given in E. W. Myers, "Algorithmic Advances for Searching Biosequence Databases," to appear in S. Suhai, Ed., *Computational Methods in Genome Research*, Plenum Press (1994)). Although it bears superficial resemblance to previous tuple-based methods, it is much more powerful. For the purpose of protein matching at high PAMs (i.e., weak or distant relationships), however, this filter is still not strong enough by itself (a fact also noted-by Myers). Thus, the main contribution of applicants is the introduction of the unit score constraint to this general method, resulting in 75% (PAM 120) to 99.9% (PAM 40) filtering of the database.

While it is easy to define optimal local alignment for a similarity measure, a suitable definition for distance is nonobvious. P. H. Sellers, in a 1981 paper, defined the pattern matching problem (by finessing a technical difficulty with the size of output being potentially quadratic) and also defined "intervals which most resembled each other locally." See P. H. Sellers, "The Theory and Computation of Evolutionary Distances: Pattern Recognition." *J. Algorithms*, pp. 359–373 (1980). W. B. Goad and M. I. Kanehisa, "Pattern Recognition in Nucleic Acid Sequences I, A General Method for Finding Local Homologies and Symmetrics," *Nucl. Acids Res.*, 10, pp. 247–263 (1982) and P. H. Sellers, "Pattern Recognition in Genetic Sequences by Mismatch Density," *Bull Math. Biol.*, 46, pp. 501–514 (1984), transformed the distance problem back to similarity, using a scoring function of the form $\epsilon$.length-distance (positive alignments therefore satisfy distance/length<$\epsilon$). However, because there are too many locally optimal (as opposed to optimal) alignments, definitions were modified (sometimes by complex procedural constraints) in order to reduce the number of such alignments. Note that an alignment with positive total score can in fact contain several negative and positive sub-alignments found this way. This happens because the Smith-Waterman method finds the highest scoring alignment, not the longest positive alignment. If length is to be taken into consideration of significance, then local alignments must be concatenated. In other words, there exists the same problem as described above: how to combine several alignments, found by using a scoring matrix minus its relative entropy, into one whose average as well as total score is high once the relative entropy is added back. It is not known in the prior art how to do this efficiently. However, as indicated earlier; the Needleman-Wunsh type method (with optimization) can be applied to each suffix of the pattern.

Chang and Lawler (cited above) defined the (k,l) substring matching problem as matching any length l substring of the pattern, allowing up to k errors. Chang and Lawler sketched both a linear expected time filter and a dynamic programming subroutine that first attempts to match the pattern as text against the local regions left by the filter (instead of considering separately all length l substrings of the pattern). Applicants now generalize this problem to allow substrings of length l or greater with at most $\epsilon$-fraction error. By applying the Smith-Waterman zero-trick to the matching statistics minus $\epsilon$ per letter, and then scanning backwards to find maximal positive regions, Applicants extend Chang and Lawler's method for (k,l) matching to ($\epsilon$,l) matching. The key is that filtering is one-dimensional, so scanning backwards does not present the same multiple choices as trying to extend a Smith-Waterman local alignment (one-dimensional diagonal embedded inside a two-dimensional matrix). The time needed for dynamic programming, though potentially very large, will be averaged out in many applications where the matching statistics filter is highly selective. Furthermore, by modifying and strengthening the filter as described above, this method can be applied to local similarity search with unit score as well as total score constraints.

The software implementation of the present invention is detailed next.

Recall that the target frequency of PAM 120 is about 33% identity, about the lowest level where one could still claim homology without additional information. The relative entropy of PAM 120 is one bit per residue, where the unit bit comes from taking logarithm to the base 2 of the target over background odds ratio. The best random local alignments of a query sequence against the protein databases have scores about 25 bits; alignments with scores lower than 20–25 bits are not distinguishable from random noise, even if they are biologically important. That is, there are hundreds if not thousands of random alignments with those scores, so any signal below 20–25 bits is essentially undetectable. This is a basic limitation of the method. What it means, is that one can ignore low-scoring alignments, or alignments that are too short to score 20 bits. A 120 PAMs alignment has to have length L=20, in order to score 20 bits (one bit per residue on average). One is therefore looking for alignments with both length (at least 20) and unit score (one bit per residue) constraints. For PAM 90, the relative entropy is about 1.4 bits, so L=15 residues are needed to yield 20 bits.

A tuple size of five (pentamers) is appropriate for database search, given that protein databases currently contain about 20 million residues (there are 3.2 million pentamers but 64 million hexamers). Both time and space are reasonable for pentamers. There turns out to be a complication: if the query sequence is too long, the best match between a random pentamer (using amino acid distribution) and it will score higher than the relative entropy! For PAM 120, Applicants divide the query sequence into blocks or segments of size S=40 that overlap by H=20, so every alignment of size L=20 is entirely contained within some block. For PAM 90, the corresponding parameters are S=80 and H=15. For PAM 40, the parameters are S=200, H=10, L=10. Parameters are in units of amino acid residues.

For each block, Applicants compute a table of pentamer scores (3.2 million in number), i.e., every pentamer's best match against the given block (allowing gaps). Only one table is kept at a time. As the database is scanned (once per block), the table of pentamer scores for the current block gives upper bounds on alignment scores. For each database sequence and each possible offset (0–4), Applicants use a new unit score maximal subvectors method to find regions of at least length L (rounded down to a multiple of 5) that satisfy the unit score constraint (respective upper bound from the table of pentamer scores), then form the union of all such regions. Smith-Waterman is performed on the union against the block. If a local alignment is found that scores 20 bits (extremely rarely), Smith-Waterman is performed for the query and database sequences.

Pseudo code to implement the foregoing in software (or firmware) is then as follows:

Given a database of known protein sequences, and given a subject biological sequence (i.e., the query sequence):
Set database tuple size to 5 (i.e., pentamers);
For each target similarity level (e.g., evolutionary distances 40, 90 or 120 PAMs), use the corresponding scoring function (PAM x matrices);
Divide subject sequence into blocks of size S that overlap by H units (so that each alignment of length L from database is entirely within some block). The parameters S, H and L are appropriately chosen for the target similarity level (PAM).
For each block do (i–v):
(i) For each possible pentamer in database do:
Compare block and pentamer,
Compute best match (alignment) score,
Store score in table, END DO;
(Table now gives upper bounds on alignment scores for current block)
(ii) For each database sequence and each possible offset (0–4) do:
Look up in the Table the alignment score upper bound for each successive pentamer of the database sequence. These form vectors of numbers, one vector for each offset.
Find contiguous subvectors of at least length L/5 (pentamers) whose mean is greater than or equal to the "relative entropy" (expected unit score) of the target similarity level (evolutionary distance). Such subvectors are infrequent. This is accomplished by the maximum Subvector Sum Method and the Unit Score Maximal Subvectors method, which together form Applicant's new Unit Score Maximum Subvector method.
(iia) Maximum subvector Sum Method: given a vector of numbers $a(1, \ldots, n)$, find a subvector $a(1, \ldots, j)$ whose sum is maximum.
let c=m=M=O:
for i=1, ..., n do:
if c+a(i) ≥ 0 then
add a (i) to c
replace m by max (m, c) and
replace M by max(M,c)
if c+a(i)<O then
set c=m=O
ENDDO;
M results as the maximum subvector sum (i.e., is the local alignment score)
(iib) Unit Score Maximal Subvectors Method: Find all subvectors whose mean is at least a given unit score and which cannot be extended.

By subtracting the given unit score from every element of the vector one can assume the unit score is zero. Two scans are needed, the first is the maximum subvector sum method augmented with a stack that holds for each nonnegative region, its rightmost decreasing prefix sums and where they occur (i.e., the maximum prefix sum for the region, then the maximum to its right, etc. each taken to be furthest to the right in case of ties). Each prefix sum is compared to the top of the stack; if it is larger, then the top of the stack is removed and this is to be repeated. If it is smaller then it is added to the stack.

The second pass is right-to-left, to determine the leftmost extension possible for each rightmost maximum that is saved on the stack (unless no subvector with the given right endpoint can be maximal). Move the left endpoint to the beginning of the next nonnegative region unless the subvector sum would turn negative. Then move the left endpoint one place at a time as long as the sum stays non negative. The total work is linear because the search for left endpoints never backs up to the right.
Every unit score maximal subvector is found by this method.
ENDDO
(iii) Form union of found regions/contiguous subvectors;
(iv) Compare union (if any) against current block to find the best local alignment by applicant's implementation of Smith-Waterman (Gotoh variation) found in Appendix I (attached).
(v) If a local alignment scores at least 20 bits then compare the subject sequence against database sequences using the Appendix subroutine, and return results.
ENDDO
return found sequence whose subvector sum was maximal (i.e., subvector a)
END ***

Figure 2:
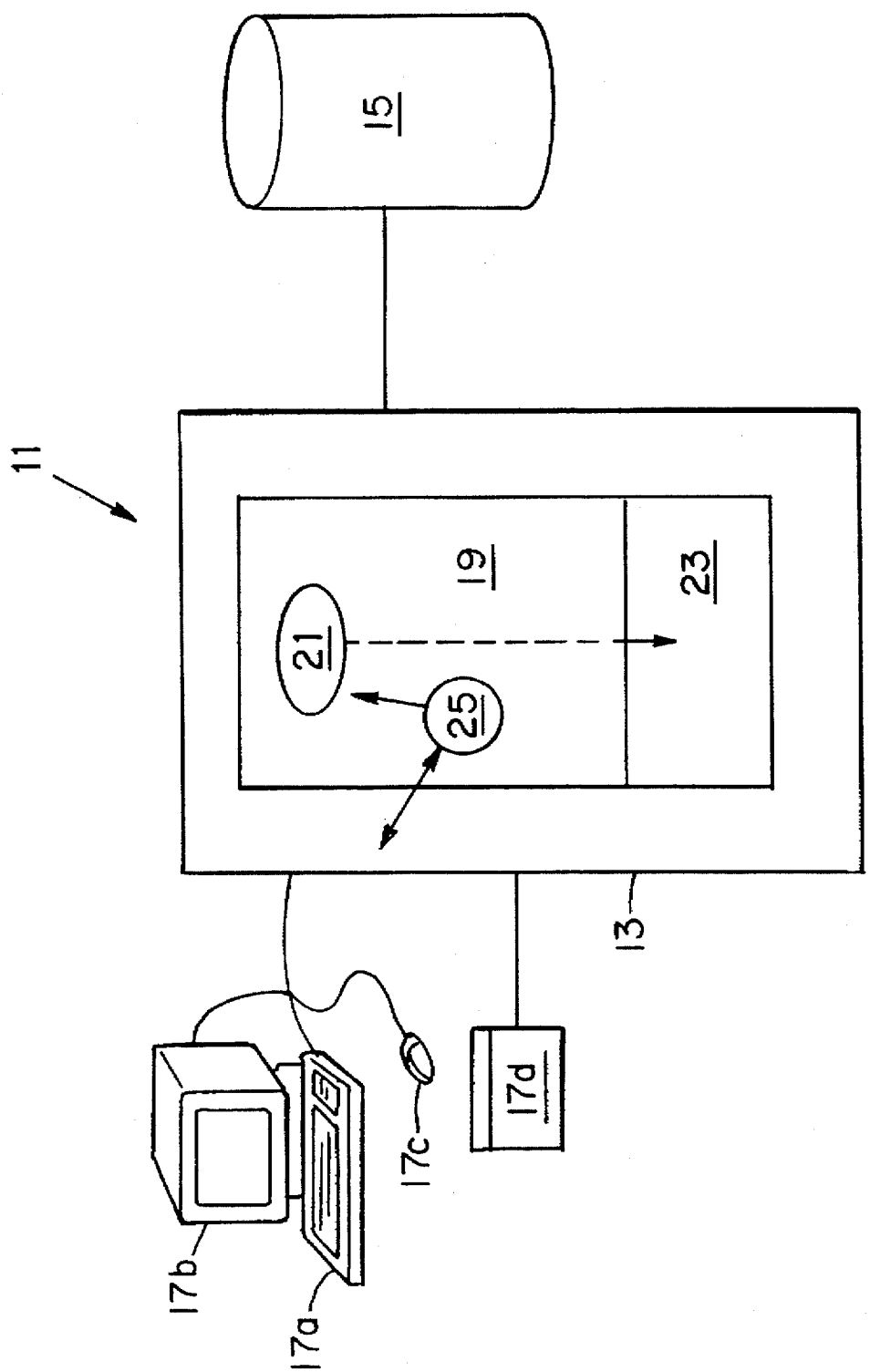
FIG. 2 is a schematic diagram of computer apparatus embodying the present invention.

In a preferred embodiment of the present invention, the foregoing is executed as a main working procedure or routine 21 in computer apparatus/system 11 illustrated in FIG. 2 and discussed next. Included in system 11 is a digital processor 13 coupled to (a) a database 15 of known sequences and (b) various I/O devices such as a keyboard 17a, mouse 17c, display monitor 17b, printer 17d and the like. Digital processor 13 is of the PC or standalone type, and has processing capabilities of at least a XX486 Intel processing chip. Other processors such as a minicomputer, parallel processor, or a networked computer are suitable. At any rate, routine 21 or an executable copy thereof is stored in working memory 19 of processor 13.

Database 15 is contained on a storage disk, magnetic tape or other memory device. Database 15 may be local or remote to processor 13. Thus, processor 13 and database 15 may be coupled across a memory card, simple cable or network link (in the local case), or a telephone line via modem and the like (in the remotely located case). Database 15 is organized as an indexed sequential, relational or other searchable database with known access protocol. The contents (known protein sequences) of the database 15, however, are subjectively interpreted in terms of functional and/or structural characteristics.

The I/O devices 17a, 17b, 17c enable user input to operate system 11. The user may be local, in which case the keyboard 17a, mouse 17c, etc., and a user interface 25 are utilized to directly provide input to processor 13. In the case of a remote user, a modem connection is used to provide user transmitted input to processor 13 and user interface 25. At any rate, to execute/run routine 21 for a subject (query) sequence, a user inputs a text string representation of the sequence and values for variables L (minimum alignment length) H (block overlap) and S (block size) (discussed above). The user interface 25 may prompt the user for this input in a menu driven or other interactive manner. Alternatively, the input may be provided in a processor command to execute routine 21, (such as for batch processing). Other means or methods for initiating a procedure call to working routine 21 in processor 13 are within the purview of one skilled in the art.

In response to the foregoing user input, processor 13 (through user interface 25) initializes and runs (executes) routine 21 for the subject sequence. Included in the initialization is the opening (accessing) of database 15. In turn, routine 21 finds the closest matching known sequence (from Database 15) to the subject sequence according to the above-described method. Routine 21 returns to processor 13 an indication of this match (a text string representation or identification name of the matching known sequence) and returns processing control to processor 13. Processor 13 stores this result in local storage memory 23 (e.g., a register or cache memory).

Preferably, the foregoing is repeated (i.e., processor 13 calls/executes working routine 21) for PAM 40 with S=200, H=10, L=10; PAM 90 with S=80, H=15, L=15; and PAM 120 with S=40, H=20, L=20 for the same subject sequence. That is, database searches are made using several scoring matrices: at least PAM 40, PAM 90, and PAM 120, in that order. Database entries containing 40 PAMs local alignments with the query sequence are not searched again for 90 PAMs or 120 PAMs alignments, etc. This way, a search using the PAM x matrix has the specific purpose of uncovering x PAMs local alignments. It is clear that distant alignments are more difficult to discover. For example, treating the query sequence as a single block usually suffices for PAM 40, because the relative entropy (2.3 bits per residue) is much higher than the noise of random pentamer scores. The total time required to do multiple PAM searches is therefore not much worse than a single search using the highest PAM, because most of the work is done at the highest PAM. Finally, Applicants note that although (affine) gap penalty is not discussed, it is included in the scoring and in the pentamer upper bounds (i.e., best match allowing gaps).

Figure 3:
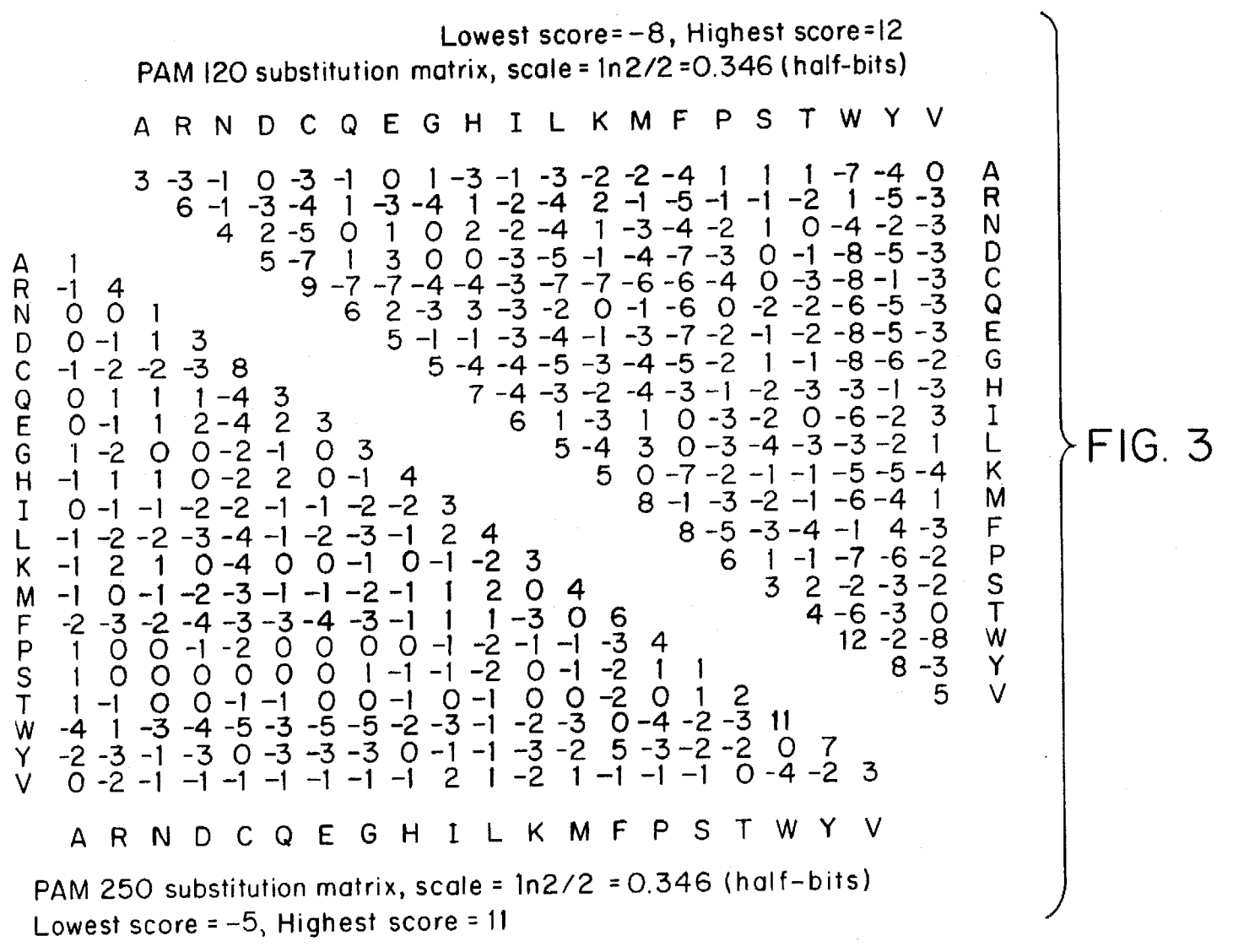

FIG. 3 is illustrative of the comparison between a PAM 120 scoring matrix and a PAM 250 scoring matrix. In the PAM 120 matrix the lowest score is −8 and the highest score is 12. In the PAM 250 matrix the lowest score is −5 and the highest score is 11.

Subsequently, local storage memory 23 of processor 13 holds a series of results (one for each run of procedure 21) for the subject sequence. At the end of processing, digital processor 13 removes from storage memory 23 and formats the series of results for output to the display monitor 17b, printer 17b, etc. as desired by the user. This is accomplished through user interface 25 by means and methods known in the art.

A computer program embodying the foregoing is now part of a package called Sequence Analyst that is being developed at Cold Spring Harbor Laboratory (Assignee). Other components include an interactive display, with scrolling windows and multiple views of the data, that uses character-cell graphics. Related alignments appear together in a screen view as desired. The computer program works effectively through both high-speed Ethernet and dial-up phone connections, The user-interface is kept simple, even though fairly powerful facilities are available for selectively hiding portions of the data(such as low scoring alignments). The basic architecture of the computer program is modular (in the preferred embodiment) such that one can input, via the user interface, a BLAST output file and the like. Redundant data (such as identical alignments against several database entries) are combined but not discarded. Such filtering can pare down a BLAST or PASTA report by a factor of ten, without losing any information. Because searching a large database can produce a massive amount of data that must be scrutinized for useful information, the importance of concise and effective visual display of the data cannot be overstated. Access to databases and powerful search facilities are available on-line as well. For example, several alignments can be merged to produce a PROSITE-type pattern, which is then compared using clp against the entire database in just seconds.

In actual use, this program produced very similar results as Smith-Waterman, only much faster and with fewer artifacts. It is faster because each separate search focuses on a narrow and well-characterized class of alignments. Because the expected score of a random pentamer against a single block is much less than the relative entropy, and in order to trigger Smith-Waterman several consecutive pentamers must score high, the filtering efficiency ranges from fairly to extremely high: 75% for PAM 120, 95% for PAM 90, >99% for PAM 40. Taking into account the overlap of blocks and table construction, the overall speedups are 2 X for PAM 120 (33% identity) and 10 X for PAM 90 (50% identity). Further improvements are expected.

Equivalents

While the invention has been particularly shown and described with reference to a preferred embodiment thereof, it will be understood by those skilled in the art that various changes in form and details may be made therein without departing from the spirit and scope of the invention as defined by the appended claims.

It is understood that user interface 25 and working routine 21 may be designed and coded (programmed) in several ways. The fundamental workings of the user interface 25 and working routine 21 are described above, bearing in mind that implementation specific details are within the purview of one skilled in the art. To that end, the foregoing description corresponding to FIG. 2 is for purposes for illustration and not limitation of the present invention.

Further it is understood that the present invention enables routine searching at multiple PAMs and various gap penalties on relatively inexpensive workstations (as opposed to massively parallel computers with thousands of processors).

Also the present invention works well for DNA or cDNA searches at the 15% error level (allowing gaps). The same user interface provides for protein or DNA searches (many-to-one alignment), multiple alignment, degenerate PCR (multiple protein fragments against DNA or cDNA databases), DNA sequencing contigs, and physical maps of clone libraries such as a map of fission yeast.

Other interfacing between the present invention and external analytical tools and the like are understood to be in the purview of one skilled in the art.

APPENDIX I

```
> /*DATA FLOW DIAGRAM of Gotoh-smith-Waterman
> 4-cell implementation by William I. Chang (wchang@cshl.org)
>
> (data flow left-to-right, top-to-bottom, unless indicated)
>
> h = horizontal-gap-open; v = vertical-gap-open; z = best
>
>
> PAM ai,bj ai,bj+1 ai,bj+2 ai,bj+3
>      |      |       |       |
>     z0 |v1 z1 |v2 z2 |v3 z3 |v4 z4
>     \| \|\| \|\| \|\| \|
>     \| \|\| \|\| \|\| \|
> z--z0' z1'<--v1'z2'<--v2'z3'<--v3'z4'<--v4' z'
>    \____^\____^\____^\____^\____/
>     \|    \|    \|    \|
> h-----h-------h-------h-------h-------h'
> (0)   (1)    (2)    (3)    (4)
> register I/O; z0-4, v1-4 are input and (indicated by ') output
> memory access; load into z, h on the left; store on the right
>       load PAM matrix[bj .. bj+3][ai]
>
> vk' = max(vk + DEL_PENALTY, zk + GAP_PENALTY)
> zk' = max(0, h(k), vk', zk-1 + PAM[bj+k-1][ai])
> h(k) = max(h(k-1) + DEL_PENALTY, zk-1' + GAP_PENALTY)
>
> z0' = z
> z' = z4'
> h' = h(4)
>
> return result; maximum z value
> */
>
>
> #define maxinto(a,b) if(a>b)b=a
> #define supermaxinto(a,b,c)c=b;if(<(temp=a))c=temp
>
>
> /*MACRO IMPLEMENTATION of 4×4 unrolling of gsw (afine gap penalty)*/
>
> #define gsw_1cell(zk_1,zk,vk,pamab,zk_1prime,zkprime)\
> {
> supermaxinto(zk + gap,vk + del,vk);\
> zkprime = zk_1 + pamab;\
> zk_1 = zk_1prime;\
> maxinto(0,zkprime);\
> supermaxinto(zk_1 + gap,h + del,h);\
> maxinto(vk,zkprime);\
> maxinto(h,zkprime);\
> maxinto(zkprime,max);\
> }/*gsw_1cell macro */
>
> #define gsw_4cell(iplus)\
> {
> h = score[iplus].h;\
> z = score[iplus].z;\
> gsw_1cell(z0,z1,v1,pamabj0[iplus],z,w);\
> gsw_1cell(z1,z2,v2,pamabj1[iplus],w,z);\
> gsw_1cell(z2,z3,v3,pamabj2[iplus],z,w);\
> gsw_1cell(z3,z4,v4,pamabj3[iplus],w,z);\
> score[iplus].h = h;\
> score[iplus].z = z;\
> z4 = z;\
> }/* gsw_4cell macro */
```

What is claimed is:

1. A computer method of comparing representations of biological sequences, comprising the steps of:

providing a source of representations of known biological sequences;

providing an indication of a subject sequence to be compared to the known sequences such that a best match is found;

using a digital processor:

(i) filtering out alignments of a certain length including fragments of the known sequences having a low average match when compared to the subject sequence and averaged across the length of the fragment, each match having a unit score constrained by a predetermined threshold, such that only alignments sufficiently matching the subject sequence on average remain, said filtering producing a remaining subset of the source of known sequences having alignments sufficiently matching the subject sequence on average; and (ii) comparing the subject sequence with each known sequence in the remaining subset to find a best match.

2. A method as claimed in claim 1 wherein the step of using a digital processor includes providing one of a processor hardware assembly coupled to the digital processor, a processor software assembly executed by the digital processor and a combination of hardware and software processor assembly for filtering out alignments and comparing the remaining subset.

3. Apparatus for comparing biological sequences comprising:

a source of known biological sequences;

computer means coupled to the source for filtering out alignments including fragments of a certain length of the known sequences having low average match when compared to a subject sequence and averaged across the length of the fragment, each match having a unit score constrained by a predetermined threshold, such that the computer means produces a remaining subset of the source of known sequences having alignments sufficiently matching the subject sequence on average; and a comparison member coupled to the computer means for comparing the subject sequence with each known sequence in the remaining subset to find a best match.

4. Apparatus for comparing biological sequences comprising:

a source of representations of known biological sequences;

a computer filter coupled to the source to receive representations of known biological sequences, the computer filter filtering out alignments including fragments of a certain length of the known sequences having low average match when compared to a representation of a subject sequence and averaged across the length of the fragment, each match having a unit score constrained by a target threshold, such that said computer filter produces a remaining subset of the source of known sequences having alignments sufficiently matching the subject sequence on average; and a comparison member coupled to the computer filter, the comparison member comparing the subject sequence with each known sequence in the remaining subset to find a best match.

5. A computer method of comparing representations of biological sequences, comprising the steps of:

providing a source of representations of known biological sequences;

providing an indication of a subject sequence to be compared to the known sequences such that a best match is found;

using a digital processor:

(i) filtering out alignments including fragments of the known sequences having a low average match when compared to the subject sequence, said filtering producing a remaining subset of the source of known sequences having alignments sufficiently matching the subject sequence on average, and said filtering comprising the steps of:

dividing the subject sequence into overlapping blocks, each block being sufficiently large to contain an alignment of length L from a known sequence; and for each block:

(a) comparing the block with each short fragment in the known sequences to form a set of fragment best matches for the block;

(b) using the set of fragment best matches, comparing the block with the known sequences to determine a set of upper bounds on alignment values;

(c) from the known sequences, determining regions of at least length L that have a mean alignment value upper bound at least as large as a target threshold;

(d) forming a union of the determined regions; and (e) comparing said union with the block in a manner that produces an indication of best local alignment; and (ii) comparing the subject sequence with each known sequence in the remaining subset to find a best match.

6. A method as claimed in claim 5 wherein the step of comparing the block with short fragments includes storing the set of fragment best matches in a table.

7. A method as claimed in claim 5 wherein the step of comparing the union with the block includes producing a local alignment score; and the step of comparing the subject sequence with the remaining subset includes comparing the subject sequence to the known sequence containing the determined regions when the local alignment score is 20 bits.

8. A method as claimed in claim 5 wherein the short fragments are pentamers; and the step of determining regions of at least length L includes rounding down to a multiple of 5.

9. A method as claimed in claim 5 wherein the step of filtering is repeated multiple times, once for each of plural similarity levels; and the target threshold is an expected unit score of the current similarity level.

10. Apparatus for comparing biological sequences comprising:

a source of known biological sequences;

computer means coupled to the source for filtering out alignments including fragments of the known sequences having low average match when compared to a subject sequence, said filtering producing a remaining subset of the source of known sequences having alignments sufficiently matching the subject sequence on average, wherein the computer means includes processor means for dividing the subject sequence into overlapping blocks, each block being sufficiently large to contain an alignment of length L from a known sequence; and for each block, the processor means (i) comparing the block with each short fragment in the known sequences to form a set of fragment best matches for the block;

(ii) using the set of fragment best matches, comparing the block with the known sequences to determine a set of upper bounds on alignment values;

(iii) from the known sequences, determining regions of at least length L that have a mean alignment value upper bound at least as large as a target threshold;

(iv) forming a union of the determined regions; and (v) comparing said union with the block in a manner that produces an indication of best local alignment; and a comparison member coupled to the computer means for comparing the subject sequence with each known sequence in the remaining subset to find a best match.

11. Apparatus as claimed in claim 10 wherein the processor means further produces a local alignment score; and the comparison member compares the subject sequence to the known sequence comprising the determined regions when the local alignment score is greater than or equal to 20 bits.

12. Apparatus as claimed in claim 10 wherein the short fragments are pentamers; and the processor means determines regions from the known sequences of at least length L including rounding down to a multiple of 5.

13. Apparatus as claimed in claim 10 wherein the processor means stores the set of fragment best matches for a given block in a table.

14. Apparatus as claimed in claim 10 wherein the processor means repeats steps (i) through (v) multiple times, once for each of plural similarity levels, and the target threshold is expected unit score of the given similarity level.

15. Apparatus as claimed in claim 14 wherein the plural similarity levels include evolutionary distances of 40 PAMs, 90 PAMs and 120 PAMs.

16. Apparatus as claimed in claim 15 wherein for similarity level of 40 PAMs, the processor means uses a block size of 200 amino acid residues, overlapping by 10, and L=20.

17. Apparatus as claimed in claim 15 wherein for similarity level of 90 PAMs, the processor means uses a block size of 80, overlapping by 15 and L=15.

18. Apparatus as claimed in claim 15 wherein for similarity level of 120 PAMs, the processor means uses a block size of 40, overlapping by 20 and L=20.

19. Apparatus for comparing biological sequences comprising:

a source of representations of known biological sequences;

a computer filter coupled to the source to receive representations of known biological sequences, the computer filter filtering out alignments including fragments of the known sequences having low average match when compared to a representation of a subject sequence, said computer filter producing a remaining subset of the source of known sequences having alignments sufficiently matching the subject sequence on average, wherein the computer filter includes processor means for dividing the subject sequence into overlapping blocks, each block being sufficiently large to contain an alignment of length L from a known sequence; and for each block, the processor means (i) comparing the block with each short fragment in the known sequences to form a set of fragment best matches for the block;

(ii) using the set of fragment best matches, comparing the block with the known sequences to determine a set of upper bounds on alignment values;

(iii) from the known sequences, determining regions of at least length L that have a mean alignment value upper bound at least as large as a target threshold;

(iv) forming a union of the determined regions; and (v) comparing said union with the block in a manner that produces an indication of best local alignment; and a comparison member coupled to the computer filter, the comparison member comparing the subject sequence with each known sequence in the remaining subset to find a best match.

* * * * *

UNITED STATES PATENT AND TRADEMARK OFFICE
CERTIFICATE OF CORRECTION

PATENT NO.  :  5,701,256
DATED       :  December 23, 1997
INVENTOR(S) :  Thomas G. Marr and William I-Wei Chang It is certified that error appears in the above-identified patent and that said Letters Patent is hereby corrected as shown below:

In column 16, line 43 (that is, line 7 of Claim 7), after "is" and before "20" insert --≥--.

Signed and Sealed this

Thirty-first Day of March, 1998

Attest:

BRUCE LEHMAN

Attesting Officer

Commissioner of Patents and Trademarks